United States Patent [19]

Heck et al.

[11] Patent Number: 4,847,426

[45] Date of Patent: Jul. 11, 1989

[54] PROCESS FOR THE PREPARATION OF 2,4-DINITROPHENYL ETHERS

[75] Inventors: Dieter Heck, Nidderau; Hartmut Heise, Bad Soden am Taunus; Manfred Hintzmann, Hofheim am Taunus, all of Fed. Rep. of Germany

[73] Assignee: Hoechst Aktiengesellschaft, Frankfurt am Main, Fed. Rep. of Germany

[21] Appl. No.: 198,285

[22] Filed: May 25, 1988

[30] Foreign Application Priority Data

May 29, 1987 [DE] Fed. Rep. of Germany ....... 3718175
Jun. 24, 1987 [DE] Fed. Rep. of Germany ....... 3720836

[51] Int. Cl.$^4$ .................... C07C 41/01; C07C 43/164
[52] U.S. Cl. ........................................ 568/587; 568/584
[58] Field of Search ................................ 568/584, 587

[56] References Cited

U.S. PATENT DOCUMENTS

| 2,048,172 | 7/1936 | Wesson | 568/584 |
| 2,988,571 | 6/1961 | MacFie et al. | 568/587 |
| 4,695,656 | 9/1987 | Reh et al. | 568/587 |

FOREIGN PATENT DOCUMENTS 3515339 10/1986 Fed. Rep. of Germany ...... 568/587

*Primary Examiner*—J. E. Evans
*Assistant Examiner*—Karen E. Kulesza

[57] ABSTRACT

A process for the preparation of 2,4-dinitrophenyl ethers of the general formula (1)

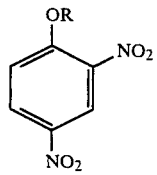

in which R denotes an alkyl($C_1$–$C_6$) or alkoxy($C_1$–$C_4$)alky($C_1$–$C_4$) group by reacting 1 mole of 2,4-dinitrochlorobenzene in the anhydrous alcohol which is required for the ether formation and is of the general formula (2)

R—OH  (2)

in which R has the abovementioned meaning, in the presence of 1.0 to 3.0 mole of an anhydrous alkali metal carbonate, at temperatures of 20° C. to 150° C., where appropriate under pressure.

7 Claims, No Drawings

PROCESS FOR THE PREPARATION OF 2,4-DINITROPHENYL ETHERS

The invention relates to a process for the preparation of 2,4-dinitrophenyl ethers by anhydrous reaction of 2,4-dinitrochlorobenzene with an alcohol in the presence of anhydrous alkali metal carbonates.

The preparation of 2,4-dinitrophenyl ethers from 2,4-dinitrochlorobenzene is in principle known from the literature. In this, the following preparation processes are mainly suggested:

Starting from 2,4-dinitrochlorobenzene, the reaction to give the 2,4-dinitrophenyl ether is carried out in the alcohol required for the ether formation with the addition of solid sodium hydroxide or potassium hydroxide or by addition of concentrated aqueous solutions of these hydroxides (Ber. 12, 765; R 21 439; Bl 27, 105; European Pat. No. 0,011,048).

Another method for the preparation of 2,4-dinitrophenyl ethers comprises reacting 2,4-dinitrochlorobenzene with an alkali metal alcoholate in the corresponding alcohol, or reacting with alkali metals in the alcohol required for the ether formation (Ber. 8, 666).

All the preparation processes hitherto described have the disadvantage that either they are not generally applicable, are industrially elaborate or are unsatisfactory in terms of industrial safety, or they provide insufficient yields and qualities owing to the formation of by-products, especially of 2,4-dinitrophenol. Thus, the reaction of 2,4-dinitrochlorobenzene with an alkali metal alcoholate in the alcohol corresponding to the alcoholate to give the corresponding 2,4-dinitrophenyl ether is virtually confined to the lower alkanols because sufficiently concentrated alcoholate solutions can be prepared only from these.

Nor is the use of alkali metals, such as sodium or potassium, in the alcohol required for the ether formation suitable, for safety reasons, for carrying out the process on an industrial scale because of the simultaneous evolution of hydrogen.

Besides the alcohol required for the ether formation and as solvent, the process most often employed in practice for the preparation of 2,4-dinitrophenyl ethers from 2,4-dinitrochlorobenzene makes use of solid alkali metal hydroxide or concentrated aqueous solutions thereof at temperatures between 10° C. and 20° C. Since more or less large amounts of 2,4-dinitrophenol, depending on the alcohol used, are always produced in this preparation process, the yields of 2,4-dinitrophenyl ethers stated in the literature are rarely above 90%. The essential disadvantage in carrying out this process industrially is, besides the reduction in yield owing to the formation of 2,4-dinitrophenol, the disposal thereof. Furthermore, during the chlorine exchange reaction 2,4-dinitrophenol is mainly present as the alkali metal salt which, because it is virtually insoluble in the solvent, is usually evident as caking on the vessel wall. However, the alkali metal salts of 2,4-dinitrophenol are, especially in the dry state, very unstable so that reactions of this type have to be carried out at the lowest possible temperature for safety reasons.

It has been found, surprisingly, that 2,4-dinitrophenyl ethers of the general formula (1)

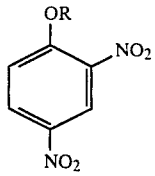

(1)

in which R denotes an alkyl($C_1$–$C_6$) or alkoxy($C_1$–$C_4$)alkyl($C_1$–$C_4$) group, can be prepared in an advantageous manner and in high yields by reacting 1 mole of 2,4-dinitrochlorobenzene in the anhydrous alcohol which is required for the ether formation and is of the general formula (2)

R—OH  (2)

in which R has the abovementioned meaning, in the presence of 1.0 to 3.0 mole, preferably 1.05 to 1.8 mole, of an anhydrous alkali metal carbonate, preferably anhydrous potassium carbonate, at temperatures of 20° C. to 150° C., preferably 40° C. to 120° C., where appropriate under pressure (depending on the alcohol of the said formula (2) which is used).

With regard to the amount of alcohol of the said formula (2) which is to be used, this depends to a considerable extent on the alcohol which is used itself, and on the solubility in the alcohol of the alkali metal carbonate which is employed. In terms of stoichiometry, just 1 mole of alcohol of the formula (2), relative to 2,4-dinitrochlorobenzene used, is sufficient. However, this may result in a suspension of alkali metal carbonate in the alcohol of the formula (2), i.e. in the reaction mixture, which is so difficult to stir that industrial implementation of the process is made difficult or virtually impossible.

It is admittedly possible to avoid this disadvantage by employing the molar ratio 2,4-dinitrochlorobenzene : alcohol (formula (2)) of 1:1 or, for example, 1:1.10, and by also adding, to achieve a suspension which can be stirred adequately, an inert diluent such as, for example, toluene or xylene. However, this procedure has the disadvantage that the inert diluent which is used has to be removed subsequently in separate process steps.

The following specific points may also be made about carrying out the process according to the invention:

It has proved expedient to allow 2,4-dinitrochlorobenzene, dissolved in the alcohol required for the ether formation, to run into a stirred suspension, which is heated to 50° C., of potassium carbonate in the said alcohol, in such a way that a reaction temperature of 60° C. is not exceeded. Depending on the alcohol used, the reaction is as a rule complete in 4–5 hours at 60° C. or at the reflux temperature. The reaction time may also be shorter or longer depending on the nature of the alcohol used and on the nature and amount of the alkali metal carbonate used and on the reaction temperature.

However, the process can also be carried out in such a way that at least 1 mole of potassium carbonate per mole of 2,4-dinitrochlorobenzene is added in portions to a stirred solution, heated to 50° C., of 2,4-dinitrochlorobenzene in the alcohol required for the ether formation, and the mixture is then stirred until reaction is complete.

In the case of alcohols which react only slightly exothermically with 2,4-dinitrochlorobenzene in the presence of potassium carbonate, it is more advantageous to mix all the reactants at once and heat under reflux until reaction is complete.

It is particularly surprising in the process according to the invention that virtually no 2,4-dinitrophenol is formed on use of at least 1 mole of potassium carbonate per mole of 2,4-dinitrochlorobenzene.

In contrast, if the same reaction is carried out with solid sodium or potassium hydroxide, the chlorine exchange can take place only with the formation of 1 mole of water per mole of 2,4-dinitrochlorobenzene, as shown in the reaction diagram

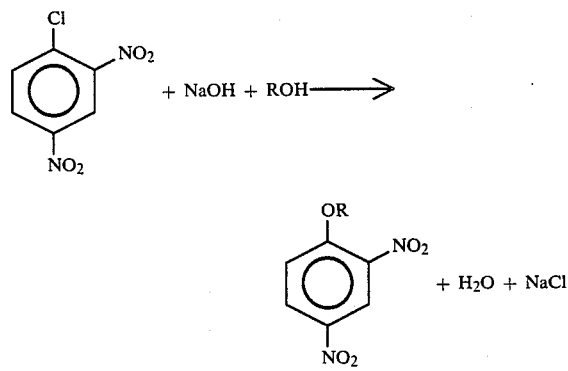

The presence of water in the reaction mixture means that part of the chlorine in the 2,4-dinitrochlorobenzene is replaced by the OH group, which results in the formation of the undesired 2,4-dinitrophenol and thus in losses in yield of the target product.

Another surprising aspect of the process is that the reaction can be easily controlled. Whereas chlorine exchange in the presence of alkali metal hydroxides or alkali metal alcoholate$ is highly exothermic, so that special measures have to be applied to make it possible to carry out the reaction safely and with control of temperature, the chlorine exchange in the presence of potassium carbonate is considerably less exothermic. Even when all the reactants are mixed at once, the temperature rises—without external cooling—only slowly from room temperature to a maximum of 70° C.

The 2,4-dinitrophenyl ethers prepared by the process according to the invention are isolated in a yield of 95–98% of theory and in a purity of 98–99%. The samples taken from the reaction mixture and examined by gas chromatography show that the formation of 2,4-dinitrophenol at temperatures of up to 60° C. is less than 0.2% relative to 2,4-dinitrochlorobenzene used.

The 2,4-dinitrophenyl ethers of the abovementioned general formula (1) are valuable precursors for the preparation of disperse dyes.

The examples which follow serve to illustrate the invention, without restricting it to them.

EXAMPLE 1

172.7 g of anhydrous potassium carbonate are introduced into a mixture of 202.5 g (1 mole) of 2,4-dinitrochlorobenzene and 157 ml of methylglycol within 1 hour in such a way that the temperature rises during this time from 25° C. to 60° C. The mixture is then stirred at 60° C. for 4 hours.

The samples then taken from the reaction mixture and examined by gas chromatography show that complete reaction has occurred and that only 0.13% of the 2,4-dinitrochlorobenzene used has reacted to 2,4-dinitrophenol.

The reaction mixture is then diluted with 320 ml of water, resulting in the salts substantially dissolving, and 2,4-dinitromethoxyethoxybenzene precipitating out. The product isolated on a suction filter funnel is washed with water to neutrality. Drying in vacuo results in 234.7 g of 2,4-dinitromethoxyethoxybenzene in a purity of >99%, which corresponds to a yield of 97.0% of theory.

EXAMPLE 2

A solution, at 40°–45° C., of 202.5 g (1 mole) of 2,4-dinitrochlorobenzene in 32 ml of methylglycol is slowly added dropwise to a suspension of 172.7 g (1.25 mole) of anhydrous potassium carbonate in 125 ml of methylglycol in such a way that a reaction temperature of 60° C. is not exceeded. The mixture is then left to stir at 60° C. for 4 hours.

The resulting reaction mixture is worked up as described in Example 1.

234.2 g of 2,4-dinitromethoxyethoxybenzene are obtained, which corresponds to a yield of 96.7% of theory. The content of undesired 2,4-dinitrophenol is 0.16% relative to 2,4-dinitrochlorobenzene used.

EXAMPLE 3

A solution, at 40° to 45° C., of 202.5 g (1 mole) of 2,4-dinitrochlorobenzene in 32 ml of methylglycol is slowly added dropwise to a suspension of 148 g (1.07 mole) of anhydrous potassium carbonate in 125 ml of methylglycol in such a way that a reaction temperature of 60° C. is not exceeded. The mixture is then left to stir at 60° C. It emerges from this that, even after a reaction time totalling 20 hours, complete reaction has not yet occurred.

2,4-Dinitrochlorobenzene is no longer detectable after heating to 100° C. and after stirring at this temperature for two hours.

223.6 g of 2,4-dinitromethoxyethoxybenzene are obtained, which corresponds to a yield of 92.3% of theory.

The content of undesired 2,4-dinitrophenol is 1.3% relative to 2,4-dinitrochlorobenzene used.

EXAMPLE 4

172.7 g (1.25 mole) of potassium carbonate are introduced in portions into a mixture of 160 ml of methanol and 205.5 g (1 mole) of 2,4-dinitrochlorobenzene within 30 minutes in such a way that the temperature rises to about 60° C. The mixture is then heated under reflux for 2 hours. Reaction is complete after this.

The product which is subsequently precipitated out by addition of 320 ml of water, isolated on a suction filter funnel and washed to neutrality with water provides, after drying, 195.6 g of 2,4-dinitroanisole of melting point 94°–95° C., which corresponds to a yield of 98.8% of theory.

EXAMPLE 5

221 g (1.6 mole) of potassium carbonate are introduced into a mixture of 300 ml of absolute ethanol and 202.5 g (1 mole) of 2,4-dinitrochlorobenzene within 30 minutes. The mixture is then heated under reflux for 6 hours.

The product which is precipitated and isolated in analogy to Example 4 provides, after drying, 206.8 g of 2,4-dinitrophenol of melting point 86°-87° C., which corresponds to a yield of 97.5% of theory.

EXAMPLE 6

A mixture of 320 ml of 1-propanol, 202.5 g (1 mole) of 2,4-dinitrochlorobenzene and 235 g (1.7 mole) of anhydrous potassium carbonate is heated at the reflux temperature for 8 hours. After the mixture has been worked up as in Example 4, 220.4 g of 1-propoxy-2,4-dinitrobenzene of melting point 34°-35° C. are obtained, which corresponds to a yield of 96.5% of theory.

EXAMPLE 7

A mixture of 320 ml of 1-butanol, 202.5 g (1 mole) of 2,4-dinitrochlorobenzene and 235 g (1.7 mole) of potassium carbonate is heated at the reflux temperature until the reaction of the dinitrochlorobenzene is complete.

The reaction is complete after 4 hours. After addition of 350 ml of water the resulting reaction mixture separates into 3 phases, and the lower (target product) and upper (1-butanol) of these phases are combined. The middle aqueous phase is discarded. Removal of the butanol by distillation results in 231.9 g of 1-butoxy-2,4-dinitrobenzene in the form of an oil with a purity of 97.6%, which corresponds to a yield of 96.6% of theory.

EXAMPLE 8

193.5 g (1.4 mole) of anhydrous potassium carbonate are introduced in portions into a mixture of 202.5 g (1 mole) of 2,4-dinitrochlorobenzene and 250 ml of ethylglycol within 30 minutes. The temperature rises during this time from 20° C. to about 45° C. The mixture is then stirred at 80° C. for 3 hours.

The reaction mixture is then diluted with 1,400 ml of water. The target product separates out as the oily lower phase. After removal of the aqueous phase, 253.7 g of 2,4-dinitro-1-(2-ethoxyethoxy)benzene with a purity of 98.3% are obtained, which corresponds to a yield of 97.4%.

Boiling point(4): 182°-184° C.

EXAMPLE 9

A mixture of 300 ml of n-butylglycol, 202.5 g (1 mole) of 2,4-dinitrochlorobenzene and 207.3 g (1.5 mole) of potassium carbonate is heated to 100° C. within 30 minutes, while stirring, and is maintained at this temperature for 4 hours. The mixture is worked up in analogy to Example 8. 268.8 g of 2,4-dinitro-1-(2-butoxyethoxy)-benzene with a purity of 98.8% are obtained, which corresponds to a yield of 93.5%.

Boiling point(4): 193°-194° C.

EXAMPLE 10

244.4 g (0.75 mole) of anhydrous cesium carbonate are introduced in portions into a mixture of 101.3 g (0.5 mole) of 2,4-dinitrochlorobenzene and 250 ml of methylglycol in such a way that the temperature rises during this time from 25° C. to 60° C. Reaction is complete after stirring at 60° C. for only 40 minutes.

Subsequently about 120 ml of methylglycol are distilled out of the mixture in vacuo, and these can be used again in the next batch. After the reaction mixture is diluted with about 400 ml of water, the target product precipitates out, while the inorganic salts dissolve.

The product isolated on a suction filter funnel and washed to neutrality with water provides, after drying, 115.6 g of 2,4-dinitromethoxyethoxybenzene (purity: 98.9%) of melting point 37° C., which corresponds to a yield of 94.5%.

EXAMPLE 11

52.0 g (0.225 mole) of anhydrous rubidium carbonate are introduced in portions into a mixture of 30.4 g (0.15 mole) of 2,4-dinitrochlorobenzene and 150 ml of methylglycol. External cooling is used to prevent a temperature of 60° C. being exceeded. A sample taken from the reaction mixture after stirring at 60° C. for 1 hour shows that reaction is already complete.

The product which is subsequently precipitated in about 500 ml of water and isolated on a suction filter funnel provides, after drying, 35.3 g of 2,4-dinitromethoxyethoxybenzene (purity: 98.7%) of melting point 36°-37° C., which corresponds to a yield of 96.0% of theory.

We claim:

1. A process for the preparation of 2,4-dinitrophenyl ethers of the formula (1)

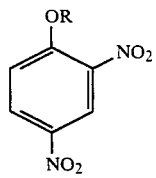

(1)

in which R denotes an alkyl($C_1$-$C_6$) or alkoxy($C_1$-$C_4$)alkyl-($C_1$-$C_4$) group, which comprises reacting 1 mole of 2,4-dinitrochlorobenzene in the anhydrous alcohol which is required for the ether formation and is of the formula (2)

R—OH (2)

in which R has the abovementioned meaning, in the presence of 1.0 to 3.0 mole of an anhydrous alkali metal carbonate, at temperatures of 20° C. to 150° C.

2. The process as claimed in claim 1, wherein 1.05 to 1.8 mole of an anhydrous alkali metal carbonate is used for the reaction.

3. The process as claimed in claim 1, wherein the reaction is carried out in the presence of anhydrous potassium carbonate.

4. The process as claimed in claim 1, wherein the reaction is carried out at temperatures of 40° C. to 120° C.

5. The process as claimed in claim 1, wherein anhydrous methanol, ethanol, propanol, butanol, methylglycol or ethylglycol is used as anhydrous alcohol of the said formula (2).

6. The process as claimed in claim 1 which is carried out in the presence of an inert diluent.

7. The process as claimed in claim 1 wherein the reaction is carried out under pressure.

* * * * *

UNITED STATES PATENT AND TRADEMARK OFFICE
CERTIFICATE OF CORRECTION

PATENT NO. : 4,847,426

DATED : July 11, 1989

INVENTOR(S) : Dieter Heck, Hartmut Heise, Manfred Hintzmann

It is certified that error appears in the above-identified patent and that said Letters Patent is hereby corrected as shown below:

In column 5, line 1, "dinitrophenol" should read --dinitrophenetol--.

Signed and Sealed this

Twelfth Day of June, 1990

Attest:

HARRY F. MANBECK, JR.

*Attesting Officer*  *Commissioner of Patents and Trademarks*